United States Patent [19]

Smith et al.

[11] Patent Number: 4,666,447

[45] Date of Patent: May 19, 1987

[54] SKIN EXPANSION DEVICE AND METHOD OF MAKING THE SAME

[75] Inventors: Gregory M. Smith, Goleta; Frederick L. Coe; Ray H. Dormandy, Jr., both of Santa Barbara, all of Calif.

[73] Assignee: Mentor Corporation, Minneapolis, Minn.

[21] Appl. No.: 696,667

[22] Filed: Jan. 30, 1985

[51] Int. Cl.⁴ .......................... A61F 2/12; A61B 19/00
[52] U.S. Cl. ......................................... 623/8; 128/1 R
[58] Field of Search ............... 623/7, 8; 128/1 R, 334; 604/83, 283, 905

[56] References Cited

U.S. PATENT DOCUMENTS

| | | | |
|---|---|---|---|
| 2,824,775 | 7/1958 | Pangman | 623/8 |
| 3,600,718 | 8/1971 | Boone | 623/8 |
| 3,663,968 | 5/1972 | Mohl et al. | |
| 3,852,833 | 12/1974 | Köneke et al. | |
| 3,860,969 | 1/1975 | Arion | 623/8 |
| 3,883,902 | 5/1975 | Lynch | 623/8 |
| 4,095,295 | 6/1978 | Lake | 623/8 |
| 4,178,643 | 12/1979 | Cox, Jr. | 623/8 |
| 4,190,040 | 2/1980 | Schulte | 128/1 |
| 4,217,889 | 8/1980 | Radovan et al. | 128/1 |
| 4,263,682 | 4/1981 | Bejarano . | |
| 4,299,227 | 11/1981 | Lincoff | 128/344 |
| 4,309,776 | 1/1982 | Berguer | 623/8 |
| 4,312,353 | 1/1982 | Shahbabian | 128/344 |
| 4,428,364 | 1/1984 | Bartolo | 128/1 |
| 4,459,318 | 7/1984 | Hyans | 427/36 |

*Primary Examiner*—Richard J. Apley
*Assistant Examiner*—David J. Isabella
*Attorney, Agent, or Firm*—Kinney & Lange

[57] ABSTRACT

An improved skin expansion device includes an inflatable envelope fluidly connected through a base thicker than the envelope to a conduit in fluid connection with an injection chamber. The base fluidly connects the conduit to the inflatable envelope through at least one fluid channel extending between a position proximate the perimeter of the base to an inwardly disposed location in fluid communication with the interior of the inflatable envelope. The conduit is connected to the base along the perimeter and in fluid communication with the fluid channel.

6 Claims, 11 Drawing Figures

U.S. Patent   May 19, 1987   Sheet 1 of 4   4,666,447
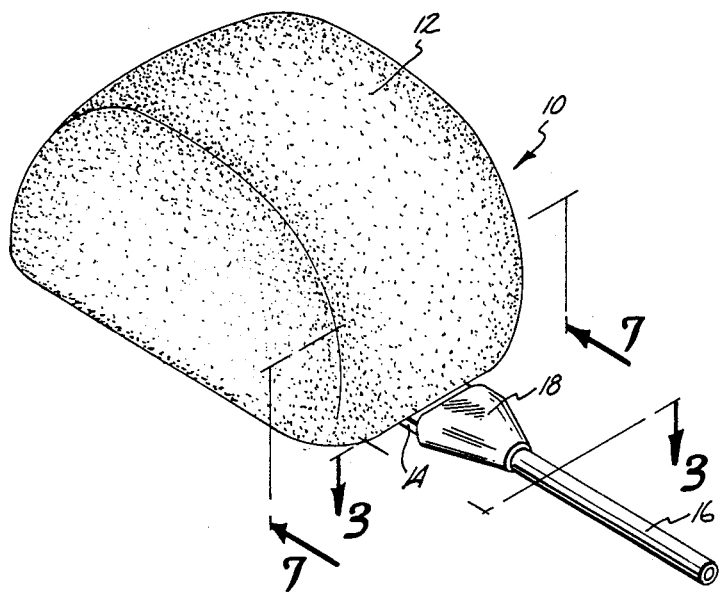
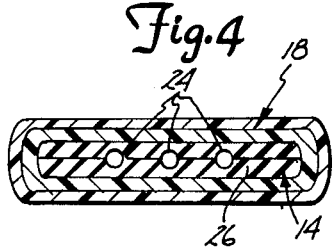
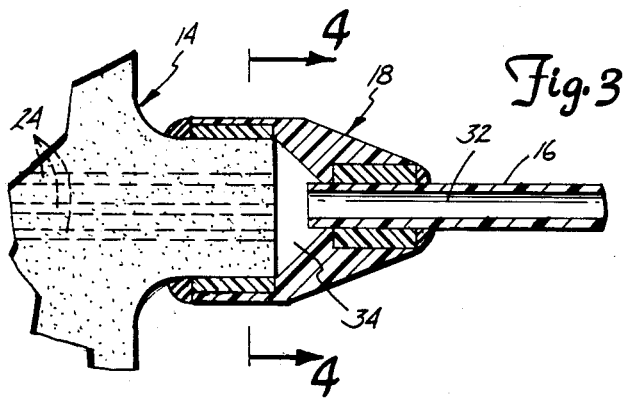
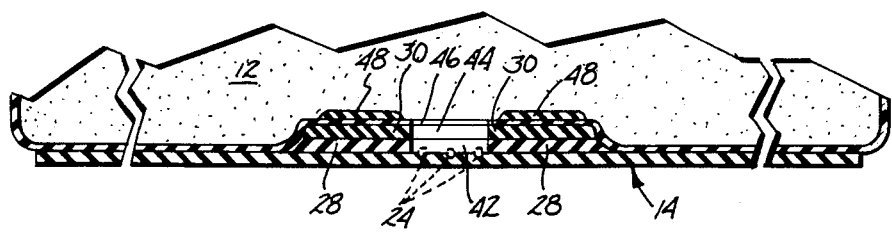

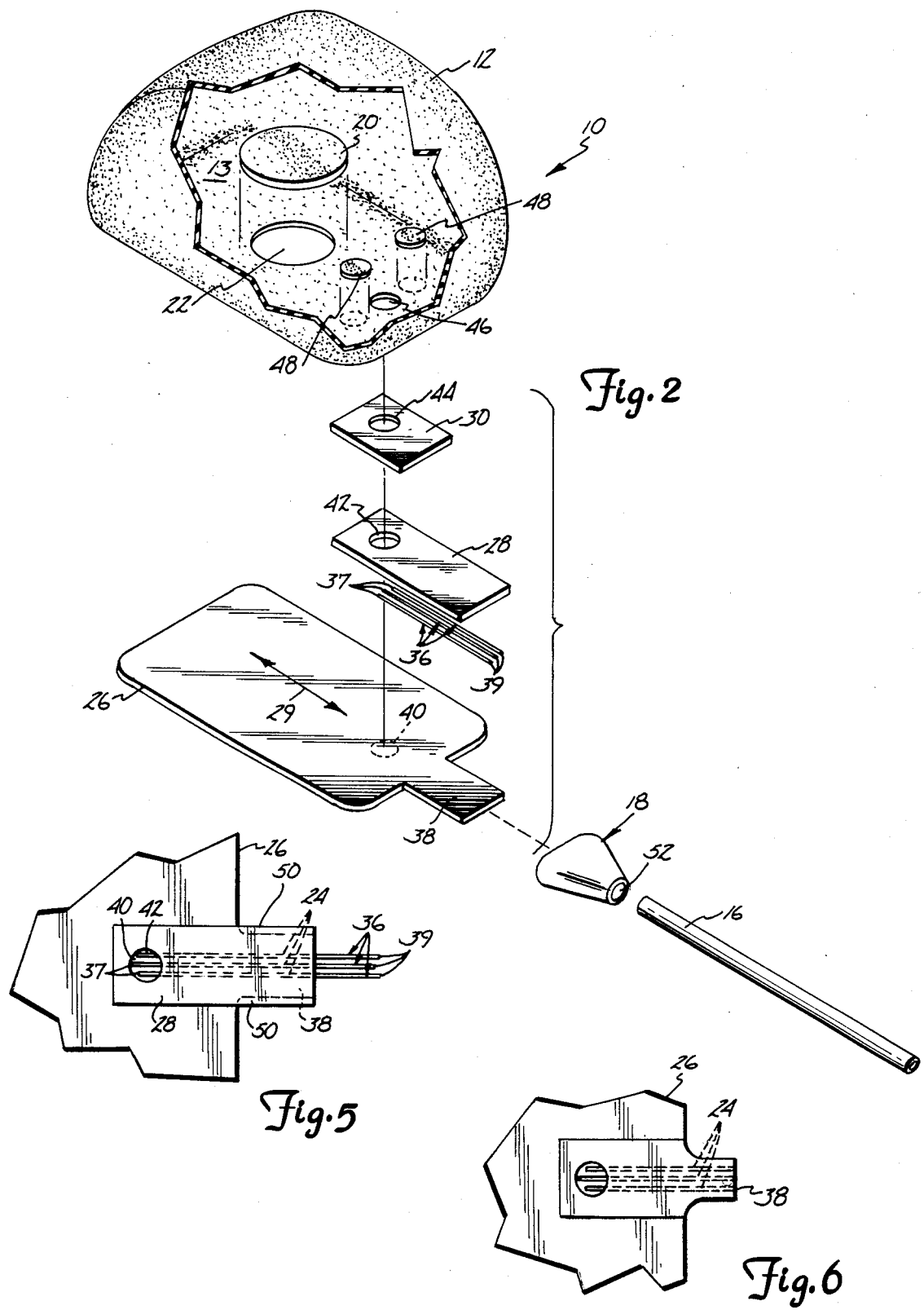

SKIN EXPANSION DEVICE AND METHOD OF MAKING THE SAME

BACKGROUND OF THE INVENTION

1. Field of the Invention

The present invention relates to implantable inflatable devices, and in particular, it relates to an implantable skin expansion device.

2. Description of the Prior Art

Present tissue expansion technology includes the implantation of a device having an inflatable envelope beneath the skin. One example of such an inflatable device is described in the Radovan et al U.S. Pat. No. 4,217,889, which is presently assigned, in part, to the same assignee as the present invention. The device of the Radovan et al patent is incrementally expanded over a period of time to develop additional tissue surface that is used for surgical reconstruction or repair.

The following patents describe other types of skin expanders and inflatable protheses:

| Inventor | U.S. Pat. No. |
| --- | --- |
| Pangman | 2,842,775 |
| Boone | 3,600,718 |
| Arion | 3,860,969 |
| Lynch | 3,883,902 |
| Lake | 4,095,295 |
| Cox, Jr. | 4,178,643 |
| Schulte | 4,190,040 |
| Lincoff | 4,299,227 |
| Berguer | 4,309,776 |
| Sahbabian | 4,312,353 |
| Bartolo | 4,428,364 |
| Hyans | 4,459,318 |

The Radovan et al. device includes an inflatable envelope attached to a base. A filling tube is glued or flanged to the inflatable envelope at one end and is connected to an injection chamber at another end which is implanted a distance away from the envelope. There are several disadvantages associated with attaching the filling tube to the inflatable envelope.

When the inflatable envelope is inflated, it rises. The area where the tubing is connected to the inflatable envelope or junction also rises. The rising junction results at times in local necrosis of surrounding tissue and erosion of the device. Also, during inflation, the rising junction of the tubing and the inflatable envelope results in the junction being moved further from the injection chamber since the injection chamber is stationarily implanted, and results in increased tensile forces on the envelope proximate the junction. The increased tensile load remains until the device is deflated.

In addition to the increased tensile load, stresses occur proximate the junction from constant flexing while the device is implanted since the filling tube and the envelope have different flexural moduli. The stresses due to the constant flexing at the junction result at times in a compromise of the envelope integrity.

After the envelope is deflated, the envelope is removed through a relatively small incision. The envelope is often simply pulled through the incision by pulling on the filling tube. The tubing and envelope may separate during removal resulting in an inconvenience to the surgeon.

SUMMARY OF THE INVENTION

The present invention includes an improved skin expanding device having an inflatable envelope, fluidly connectable to an injection chamber. The improvement includes a base thicker than the envelope having at least one fluid channel fluidly connectable to the injection chamber and extending through the base from a position proximate the perimeter of the base to a location within the perimeter of the base to fluidly communicate with the interior of the inflatable envelope.

The present invention by including a base with a fluid channel permits connecting a fill tube to the base at one end and connecting the fill tube to the injection chamber. The fill tube and the base are the two strongest components of the device and together create a more structurally reliable device able to withstand higher shock loads and longer cyclic loadings and facilitate removal of the device from a patient through a small incision by pulling on the fill tube. Removal of the skin expander is facilitated because the base tends to fold into a more removable shape when pulled by the attached fill tube, allowing easier removal through small incisions. In addition, stresses on the inflatable envelope resulting from the connection of the fill tube are eliminated, and when the inflatable envelope is inflated, the fill tube remains in substantially the same plane as it was when implanted thereby minimizing tissue necrosis and erosion of the device.

BRIEF DESCRIPTION OF THE DRAWINGS

FIG. 1 is a perspective view of the skin expansion device of the present invention.

FIG. 2 is a exploded perspective view of the skin expansion device of the present invention.

FIG. 3 is a cross-sectional view illustrating the attachment of the filling tube to a base of the device taken along the line 3—3 in FIG. 1.

FIG. 4 is a cross-sectional view showing the layers comprising the base and the fluid channels in the base taken along the line 4—4 in FIG. 3.

FIG. 5 is a top view with a slip cover washer and inflatable envelope removed illustrating the positioning of the wires between the base and a slip cover when the channels are being formed.

FIG. 6 is a top view with the washer and inflatable envelope also removed illustrating the slip cover having been trimmed.

FIG. 7 is a cross-sectional view showing the layers comprising the base and the fluid channels in the base taken along the line 7—7 in FIG. 1.

DETAILED DESCRIPTION OF THE PREFERRED EMBODIMENTS

Figure 8:
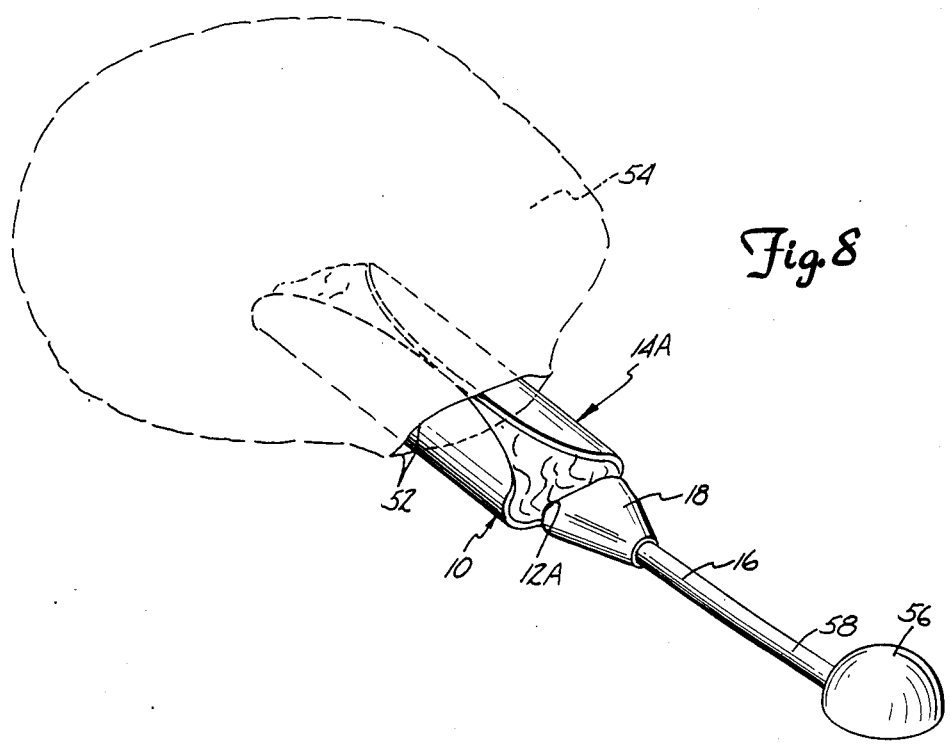
FIG. 8 is a perspective view of an alternative embodiment illustrating insertion and removal of the skin expansion device having a base with a circular configuration into and from an incision in a pocket formed under the skin.

The improved skin expansion device is generally indicated at 10 in FIGS. 1 and 2. Skin expansion by an inflatable prosthesis is well known in the art, having initially been described in the Radovan et al U.S. Pat. No. 4,217,889, which is presently assigned, in part, to the same assignee as the present application, and is hereby incorporated by reference. The skin expander of the Radovan et al patent has been used satisfactorily for both creating skin grafts and for breast reconstruction following radical mastectomy.

The present invention is an improved skin expansion device having an inflatable envelope 12 attached to an improved base 14. Fluid for inflating the envelope is conveyed to and from the envelope 12 through the base 14 via preferably a fill tube 16 connected to the base 14, preferably by a connecting boot 18.

The inflatable envelope 12 is an integral shell having a bottom wall section 13 for attachment to the base 14 and is made in a well known manner of a biocompatible medical grade silicone polymer. A patch 20 having an uncured bottom layer is required to cover a mandrel hole 22 created during the production of the envelope on a mandrel (not shown).

The base 14 includes a plurality of fill channels 24, which are best illustrated in FIGS. 3 through 7. The base 14 includes a substantially flat, vulcanized base sheet 26 as best illustrated in FIG. 2, preferably having an upper unvulcanized layer of silicone polymer, a cover slip 28 made of a top layer of vulcanized silicone polymer and a bottom layer of unvulcanized silicone polymer, and cover slip washer 30 made of unvulcanized silicone polymer. The cover slip 28 and the base sheet 26 are joined together to form the fill channels 24, as will be discussed subsequently. The base sheet 26 is typically 3 to 4 times, and at the very least twice, the thickness of the inflatable envelope 12. The base sheet 26 is substantially non-extensible preferably with minimum stretching characteristics in the direction indicated by arrow 29. The non-extensible base permits controlled expansion of the envelope 12 as discussed in the Radovan et al. patent. In one working example, the base sheet 26 was approximately 1.0±5 mm thick, the cover slip 28 was approximately 0.016 inches thick and the cover slip washer was approximately 0.020 inches thick. Although the base 14 is described in detail, other alternate embodiments containing fill channels are includable within the scope of the present invention.

Referring to FIGS. 3 and 4, the fill tube 16 is securely attached to the boot 18, such as with an adhesive, and has a fluid channel 32 in fluid communication with a manifold chamber 34 of the boot 18. The boot 18 in turn is securely attached to the base 14, also by an adhesive. The manifold chamber 34 is in fluid communication with the fill channels 24 so that the fluid flows unobstructed between the fluid channels 24 of the base 14 and the fluid passage 32 of the filling tube 16.

To manufacture the improved skin expansion device of the present invention, a plurality of wires 36 are positioned on the top surface of the sheet 26. The sheet 26 has an integral forward projecting tongue section 38. The wires 36 are positioned on the top unvulcanized layer of the sheet 26 such that first ends 32 of the wires extend inwardly to a location on the sheet 26 designated by reference character 40, and second ends 39 extend outwardly beyond the edge of the tongue section, as illustrated in FIG. 5. The wires 36 are spaced apart from each other preferably in a substantially parallel arrangement. The cover slip 28 includes an aperture 42 that is disposed over the end portions 37 of the wires 36. In one working embodiment, the wires 36 were spaced apart approximately 0.07±0.1 inches and were approximately 0.028 inches in diameter. The tongue section was approximately 0.32±0.02 inches wide.

The cover slip washer 30 is then positioned on top of the cover slip 28 as illustrated in FIG. 2. The cover slip washer 30 also includes an aperture 44 that is substantially coaxially aligned with the aperture 42 of the cover slip 28.

The inflatable envelope 12 also includes an aperture 46 in the bottom wall section 13 and is positioned over the base 14 such that the aperture 46 is aligned with the apertures 44 and 42 and the bottom wall section 13 is positioned over the base sheet 26 with the tongue section 38 extending beyond the inflatable envelope 12.

Preferably, a pair of anti-occlusion disks 48 are placed within the envelope 12 on opposite sides of the aperture 46. The disks 48 are made of a silicone polymer and have a bottom unvulcanized layer. In one working example, the aperture 46 was 7.0±0.5 mm in diameter and the anti-occlusion disks were also 7.0±0.5 mm in diameter and approximately 0.016 inches thick, and were spaced from the aperture 46 approximately 0.04 inches. The disks 48 prevent the envelope 12, when being deflated, from occluding the aperture 46 thereby avoiding difficulties in deflating the device of the present invention.

The assembled skin expansion device of the present invention is then heated to a temperature that causes flow of the unvulcanized layers of the base sheet 26, the anti-occlusion disks 48, the patch 20, the cover slip 28 and the unvulcanized cover slip washer 30 so that the base sheet 26, cover slip 28, cover slip washer 30, envelope 12, patch 20 and anti-occlusion disks 48 adhere to one another. In addition, the unvulcanized silicone polymer of the cover slip 28 and base sheet 26 flows around the wires 36 to form the fill channels 24.

The wires 36 are then removed, forming fill channels 24, as illustrated in FIG. 6. The end of the tongue section 38 of the base sheet 26 and the cover slip 28 that extends over the tongue section 38 are trimmed. In addition, edges 50 of the cover slip 28, as illustrated in FIG. 5, are trimmed to form a finished end, as illustrated in FIG. 6.

The boot 18 is then adhesively secured to the tongue section 38 and the filling tube is inserted into an aperture 52 of the boot 18 and is adhesively secured to surfaces forming the aperture 52.

As illustrated in FIG. 7, which is a sectional view taken along the line 7—7 in FIG. 1, the base sheet 26, the cover slip 28 and the cover slip washer 30 form an integral base 14 having a plurality of fill channels 24, their position indicated by broken lines 24, that are in fluid communication with the aligned apertures 42, 44 and 46 and the interior of the envelope 12. As also illustrated in FIG. 7, the anti-occlusion disks 48 extend above the upper edge of the aperture 46 of the envelope 12 to prevent occlusion when deflation of the envelope occurs prior to removal of the skin expander from a patient.

FIGS. 8 through 11 illustrate the improved skin expansion device 10 in use. (FIG. 8 illustrates a skin expansion device having a circular base 14A and an envelope 12 also having a generally circular configuration as compared to the rectangular base configuration illustrated in FIGS. 1 and 2.) The skin expansion device 10 is inserted through an incision 52 with the base 14A folded over the envelope 12A in a deflated state, as illustrated in FIG. 8. Before the skin expander is inserted through the incision 52, a pocket 54 is made beneath the skin and subcutaneous layer. An injection chamber 56, such as described in the Radovan et al patent, previously mentioned above, having a connecting tube 58, is attached to the fill tube 16 by a suitable connector (not shown).

Figure 9:
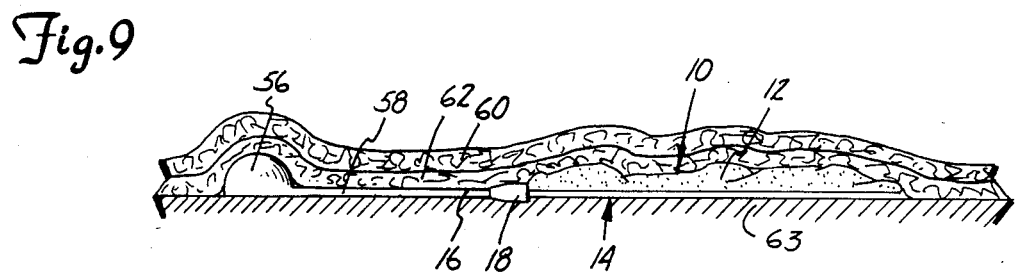
FIGS. 9-11 are partial sectional views of the skin expansion device implanted, illustrating the unchanged position of the connection of the fill tube to the base and the unchanged position of the fill tube during inflation.
Figure 10:
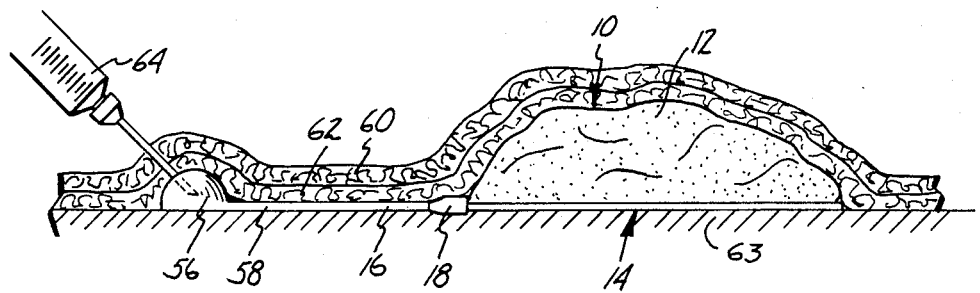
Figure 11:
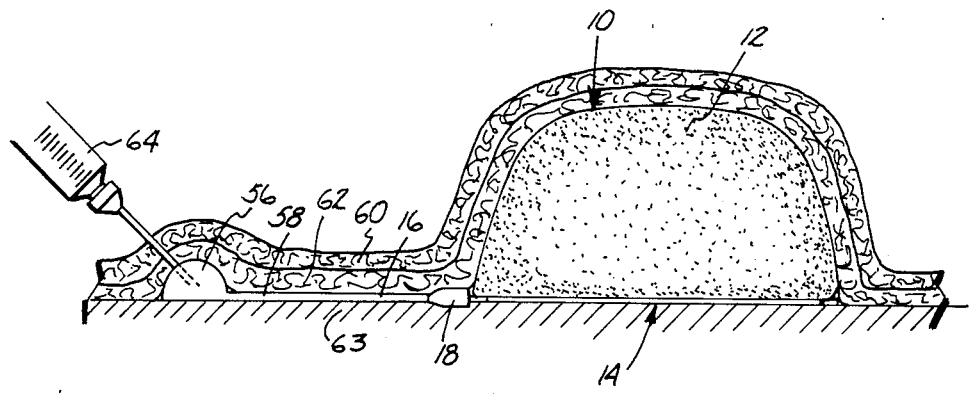

As illustrated in FIG. 9, the injection chamber 56, the connecting tube 58, the fill tube 16, the boot 18 and the skin expansion device 10 are all implanted under the skin 60 and the subcutaneous layer 62 on top of underlying tissue and muscle 63. The chamber is filled until the tissue is under slight pressure and then the tubing is connected to the injection port. A hypodermic syringe 64 is then used on subsequent serial inflation to pierce the injection chamber 56 by puncturing the skin 60, subcutaneous layer 62 and the injection chamber 56. A saline solution is injected using the hypodermic syringe 64 into the injection chamber 56 causing flow through the connecting tube 58 and the fill tube 16 through the boot 18 and into the fill channels 24 of the base 14 into the interior of the envelope 12. The envelope 12 inflates expanding the skin 60 and the subcutaneous layer 62, as illustrated in FIG. 10. The injections occur over a period of time, typically several weeks, allowing the skin to stretch over an increasingly larger inflated envelope 12, as illustrated in FIGS. 10 and 11.

As the envelope 12 is inflated, the connecting tube 58, the fill tube 16 and the boot 18 remain in the same plane as initially implanted in FIG. 9. Unlike prior art devices, the connecting tubing 58, the fill tube 16 and the connection of the fill tube 16 to the skin expander 10 by the boot 18 does not rise during inflation, thereby reducing tissue necrosis and erosion of the device. Further, since the connecting tubing 58, fill tube 16 and boot 18 do not rise, the connection represented by the boot 18 is not moved further from the injection chamber 56, eliminating the stresses the inflatable envelope that have occurred in prior art devices.

FIG. 8 also illustrates the removal of the skin expansion device 10 of the present invention. To remove the skin expansion device 10, an incision smaller than the width of the base is made, and the base folded back over (after deflation) and removed by pulling on the fill tube 16. With the fill tube 16 attached directly to the base, the expansion device is withdrawn in a much easier manner than prior art devices.

Although a specific embodiment of the present invention has been described, it will be understood by those skilled in the art that the various dimensions and shape of the skin expansion device 10 of the present invention may be varied to fit particular needs of the patient. For example, the base sheet 26 may be reinforced with a fabric mesh such as described in the Radovan et al patent. Additional layers of sheeting material may be used to form the base sheet 26, or the thickness of the base sheet 26 may be varied depending on the particular application of the device of the present invention but always having a substantially non-extensible characteristic.

In addition, the width and length of the base sheet 26 can be reduced to simply accommodate the formation of the fill channels 24 by forming the base 14 and by attaching the base 14 to the envelope in substantially the same manner as described above. In a further variation of the device of the present invention, the fill channels can be formed into the bottom wall section 13 of the inflatable envelope 12.

Furthermore, the configuration of the fill tube can be changed or integrated into the expansion device and the shape, number and layout of the fill channels can be varied. In addition, the injection chamber, or multiple injection chambers, can be integrated into the base 14 and directly connected to the fill channels without the use of fill tube 16. The fill channels may be designed to enter the interior of the inflatable envelope 12 at disparate locations, further reducing the likelihood of occlusion during deflation.

In addition, slight protruberances, instead of the anti-occlusion disks 48, may be in situ incorporated about the envelope aperture 46 to avoid occlusion by the inflatable envelope when withdrawing fluid during deflation.

In summary, the device of the present invention provides a number of advantages.

1. A fluid path is incorporated into the base of the device, avoiding stress concentrations in the material of the inflatable envelope 12 and providing a stronger junction between the fill tube and the skin expansion device.

2. The fluid path remains in the same plane as when implanted in a deflated state, even after the skin expander is inflated, minimizing the likelihood of fluid path disruption or increasing tensile load on the fill tube/skin expansion device connection during inflation.

3. A flat bottom surface of the base is preferably retained, avoiding stress concentrations on underlying tissue such as would occur with prior art inflatable devices that have tubing leading to a bottom entry site.

4. The multiple fill channels make occlusion of the fill path to the envelope less likely.

5. Removal of the skin expander is facilitated by the attachment of the fill tube directly to the base providing more extraction force to be applied to the base in the direction of pull which permits easier withdrawal through a small incision.

Although the present invention has been described with reference to preferred embodiments, workers skilled in the art will recognize that changes may be made in form and detail without departing from the spirit and scope of the invention.

What is claimed is:

1. An improved implantable expansion device having an inflatable envelope with a fluid retaining interior for implantation, the envelope being fluidly connected by a fill tube to a remote implantable injection site, the improvement comprising:
said envelope being fixedly attached to a substantially non-extensible base having a base perimeter and said base having a tongue portion extending beyond said base perimeter said fluid retaining, the channel being formed in said base and extending from said opening through the base to a position proximate a perimeter of the base into said tongue portion and fluidly connectable to the injection site from the position proximate the perimeter so that inflating fluid flows between the injection site through the fill tube into said tongue portion through said channel and said opening and into the interior of the envelope, such that when the envelope is inflated after implantation, the base and the fill tube remain in substantially the same plane as when implanted.

2. The device of claim 1 wherein the base includes a plurality of fluid channels.

3. The device of claim 2 wherein the fluid channels have first ends disposed inwardly in the base and the envelope has an aperture in fluid communication with the second ends of the fluid channels and means for preventing occlusion positioned proximate the aperture to prevent the envelope from occluding the aperture during deflation.

4. The device of claim 3 wherein the means for preventing occlusion includes at least two spaced-apart sections of sheet material secured to the bottom wall portion of the envelope proximate the aperture.

5. An improved implantable expansion device having an inflatable envelope with a fluid retaining interior for implantation, the envelope being in fluid communication with an injection site, the improvement comprising:
   said envelope being fixedly attached to a substantially non-extensible base having a base perimeter, and said base having a tongue portion extending beyond said base perimeter;
   said base having at least one fluid channel with an opening communicating with said fluid retaining interior, said channel being formed in said base and extending from said opening through said base into said tongue portion and fluidly connectable to the injection site from a position proximate said base perimeter so that inflating fluid-flows between the injection site through a fill tube into said tongue portion through said channel and said opening into the interior of the envelope,
   and means for positioned proximate said opening for preventing the envelope from occluding the opening during inflation.

6. The device of claim 5 wherein the means for preventing occlusion includes at least two spaced-apart sections of sheet material secured to the bottom wall portion of the envelope proximate the opening.

* * * * *